(12) United States Patent
Ghahary et al.

(10) Patent No.: US 11,686,737 B2
(45) Date of Patent: *Jun. 27, 2023

(54) DISSOLVED PROTEIN ARTHRITIS MARKERS

(71) Applicant: The University of British Columbia, Vancouver (CA)

(72) Inventors: Aziz Ghahary, Vancouver (CA); Wolodymyr Walter Peter Maksymowych, Edmonton (CA); Ruhangiz Taghi Kilani, Vancouver (CA)

(73) Assignee: THE UNIVERSITY OF BRITISH COLUMBIA

( * ) Notice: Subject to any disclaimer, the term of this patent is extended or adjusted under 35 U.S.C. 154(b) by 310 days.

This patent is subject to a terminal disclaimer.

(21) Appl. No.: 16/868,447

(22) Filed: May 6, 2020

(65) Prior Publication Data

US 2021/0055308 A1 Feb. 25, 2021

Related U.S. Application Data

(63) Continuation of application No. 15/785,205, filed on Oct. 16, 2017, now Pat. No. 10,677,804, which is a continuation of application No. 12/637,730, filed on Dec. 14, 2009, now Pat. No. 9,791,458, which is a continuation of application No. 12/300,118, filed as application No. PCT/CA2007/000817 on May 9, 2007, now abandoned.

(60) Provisional application No. 60/798,712, filed on May 9, 2006.

(51) Int. Cl.
*G01N 33/68* (2006.01)
*G01N 33/564* (2006.01)
*A61P 19/02* (2006.01)

(52) U.S. Cl.
CPC .......... *G01N 33/6893* (2013.01); *A61P 19/02* (2018.01); *G01N 33/564* (2013.01); *G01N 2800/102* (2013.01)

(58) Field of Classification Search
CPC ... G01N 2800/102; G01N 33/00; A61P 29/00; A61P 37/00
See application file for complete search history.

(56) References Cited

U.S. PATENT DOCUMENTS

| | | | | |
|---|---|---|---|---|
| 9,079,947 B2* | 7/2015 | Marotta | ............. | G01N 33/6893 |
| 9,791,458 B2* | 10/2017 | Ghahary | ............ | G01N 33/6893 |
| 10,677,804 B2* | 6/2020 | Ghahary | ............ | G01N 33/6893 |
| 10,995,136 B2* | 5/2021 | Marotta | ................. | A61P 43/00 |

* cited by examiner

*Primary Examiner* — Theodore R. Howell
(74) *Attorney, Agent, or Firm* — Todd Lorenz

(57) ABSTRACT

Methods and kits for diagnosing arthritis are provided. The methods may involve detection of 14-3-3 eta or gamma proteins in a sera or synovial fluid sample.

14 Claims, 7 Drawing Sheets

Specification includes a Sequence Listing.

SEQUENCE LISTING

```
<160> NUMBER OF SEQ ID NOS: 16

<210> SEQ ID NO 1
<211> LENGTH: 242
<212> TYPE: PRT
<213> ORGANISM: Homo sapiens
<220> FEATURE:
```

<223> OTHER INFORMATION: 14-3-3 beta protein; brain protein 14-3-3 beta
      isoform
<220> FEATURE:
<223> OTHER INFORMATION: Alternate nomenclature: Tyrosine
      3-monooxygenase/tryptophan 5-monooxygenase activation protein,
      beta isoform, YWHAB

<400> SEQUENCE: 1

Met Thr Met Asp Lys Ser Glu Leu Val Gln Lys Ala Lys Leu Ala Glu
1               5                   10                  15

Gln Ala Glu Arg Tyr Asp Asp Met Ala Ala Met Lys Ala Val Thr
                20                  25                  30

Glu Gln Gly His Glu Leu Ser Asn Glu Glu Arg Asn Leu Leu Ser Val
                35                  40                  45

Ala Tyr Lys Asn Val Val Gly Ala Arg Arg Ser Ser Trp Arg Val Ile
            50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly

<210> SEQ ID NO 2
<211> LENGTH: 246
<212> TYPE: PRT
<213> ORGANISM: Homo sapiens
<220> FEATURE:
<223> OTHER INFORMATION: 14-3-3 gamma protein
<220> FEATURE:
<223> OTHER INFORMATION: Alternate nomenclature: Tyrosine
      3-monooxygenase/tryptophan 5-monooxygenase activation protein,
      gamma isoform, YWHAG

<400> SEQUENCE: 2

Met Val Asp Pro Glu Gln Leu Val Gln Lys Ala Arg Leu Ala Glu Gln
1               5                   10                  15

Ala Glu Gly Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
            35                  40                  45

```
Tyr Lys Asn Val Val Gly Ala Arg Arg Ser Ser Trp Arg Val Ile Ser
 50                  55                  60

Ser Ile Glu Gln Lys Thr Ser Ala Asp Gly Asn Glu Lys Ile Glu Met
 65                  70                  75                  80

Val Arg Ala Tyr Arg Glu Lys Val Glu Lys Glu Leu Glu Ala Val Cys
                 85                  90                  95

Gln Asp Val Leu Ser Leu Val Asp Asn Tyr Leu Tyr Lys Asn Cys Ser
                100                 105                 110

Glu Thr Gln Tyr Glu Arg Lys Asp Leu Tyr Leu Lys Met Lys Gly Asp
                115                 120                 125

Tyr Tyr Arg Tyr Leu Ala Glu Val Ala Thr Gly Glu Lys Arg Gly Asp
130                 135                 140

Val Val Glu Ser Ser Glu Lys Ala Tyr Ser Glu Arg Glu Ile Ser Lys
145                 150                 155                 160

Glu His Met Gln Pro Thr His Pro Ile Arg Leu Gly Leu Ala Leu Asn
                165                 170                 175

Tyr Ser Val Phe Tyr Tyr Glu Ile Gln Asn Ala Pro Glu Gln Ala Cys
                180                 185                 190

His Leu Ala Lys Thr Glu Phe Glu Asp Ala Ile Ala Glu Leu Asp Thr
                195                 200                 205

Leu Asn Glu Glu Ser Tyr Lys Asp Ser Thr Leu Ile Met Gln Leu Leu
210                 215                 220

Arg Asp Asn Leu Thr Leu Trp Thr Ser Asp Gln Gln Asp Asp His Asp
225                 230                 235                 240

Gly Gly Glu Gly Asn Asn
                245

<210> SEQ ID NO 3
<211> LENGTH: 244
<212> TYPE: PRT
<213> ORGANISM: Homo sapiens
<220> FEATURE:
<223> OTHER INFORMATION: 14-3-3 eta protein
<220> FEATURE:
<223> OTHER INFORMATION: Alternate nomenclature: Tyrosine
      3-monooxygenase/tryptophan 5-monooxygenase activation protein,
      eta isoform, YWHAH;
<220> FEATURE:
<223> OTHER INFORMATION: brain protein 14-3-3, eta isoform tyrosine
      3-monooxygenase/tryptophan 5-monooxygenase activation
      protein 1; YWHA1

<400> SEQUENCE: 3

Met Gly Asp Arg Glu Gln Leu Leu Gln Arg Ala Arg Leu Ala Glu Gln
 1               5                  10                  15

Ala Glu Arg Tyr Asp Asp Met Ala Ser Ala Met Lys Ala Val Thr Glu
                 20                  25                  30

Leu Asn Glu Pro Leu Ser Asn Glu Asp Arg Asn Leu Leu Ser Val Ala
                 35                  40                  45

Tyr Lys Asn Val Val Gly Ala Arg Arg Ser Ser Trp Arg Val Ile Ser
 50                  55                  60

Ser Ile Glu Gln Lys Thr Met Ala Asp Gly Asn Glu Lys Lys Leu Glu
 65                  70                  75                  80

Lys Val Lys Ala Tyr Arg Glu Lys Ile Glu Lys Glu Leu Glu Thr Val
                 85                  90                  95

Cys Asn Asp Val Leu Ser Leu Leu Asp Lys Phe Leu Ile Lys Asn Cys
                100                 105                 110

Asn Asp Phe Gln Tyr Glu Ser Lys Val Phe Tyr Leu Lys Met Lys Gly
```

```
                    115                 120                 125
Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
                180                 185                 190

Ala Cys Leu Leu Ala Lys Gln Ala Phe Asp Asp Ala Ile Ala Glu Leu
                195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Glu
225                 230                 235                 240

Glu Ala Gly Glu

<210> SEQ ID NO 4
<211> LENGTH: 255
<212> TYPE: PRT
<213> ORGANISM: Homo sapiens
<220> FEATURE:
<223> OTHER INFORMATION: 14-3-3 epsilon protein
<220> FEATURE:
<223> OTHER INFORMATION: Alternate nomenclature: Tyrosine
      3-monooxygenase/tryptophan 5-monooxygenase activation protein,
      epsilon isoform, YWHAE epsilon isoform

<400> SEQUENCE: 4

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
            115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
```

```
                210                 215                 220
Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 5
<211> LENGTH: 247
<212> TYPE: PRT
<213> ORGANISM: Homo sapiens
<220> FEATURE:
<223> OTHER INFORMATION: 14-3-3 sigma protein
<220> FEATURE:
<223> OTHER INFORMATION: Alternate nomenclature: stratifin

<400> SEQUENCE: 5

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
                20                  25                  30

Gly Glu Glu Leu Ser Cys Glu Glu Arg Asn Leu Leu Ser Val Ala Tyr
            35                  40                  45

Lys Asn Val Val Gly Gly Gln Arg Ala Ala Trp Arg Val Leu Ser Ser
50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln
                245

<210> SEQ ID NO 6
<211> LENGTH: 245
<212> TYPE: PRT
<213> ORGANISM: Homo sapiens
<220> FEATURE:
<223> OTHER INFORMATION: 14-3-3 tau protein
<220> FEATURE:
<223> OTHER INFORMATION: Alternate nomenclature: Tyrosine
      3-monooxygenase/tryptophan 5-monooxygenase activation protein, tau
      isoform, YWHAQ 14-3-3 protein, T-cell 14-3-3-theta HS1
```

<400> SEQUENCE: 6

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 7
<211> LENGTH: 245
<212> TYPE: PRT
<213> ORGANISM: Homo sapiens
<220> FEATURE:
<223> OTHER INFORMATION: 14-3-3 zeta protein
<220> FEATURE:
<223> OTHER INFORMATION: Alternate nomenclature: Tyrosine
      3-monooxygenase/tryptophan 5-monooxygenase activation protein,
      zeta isoform, YWHAZ; brain protein 14-3-3, zeta isoform

<400> SEQUENCE: 7

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 8
<211> LENGTH: 3015
<212> TYPE: DNA
<213> ORGANISM: Homo sapiens
<220> FEATURE:
<223> OTHER INFORMATION: 14-3-3 beta cDNA (NM_139323) 3015 nt

<400> SEQUENCE: 8
gcggaagtgg agctaccgcc accgccgccg ccgattccgg agccggggta gtcgccgccg      60
ccgccgccgc tgcagccact gcaggcaccg ctgccgccgc ctgagtagtg ggcttaggaa     120
ggaagaggtc atctcgctcg gagcttcgct cggaagggtc tttgttccct gcagccctcc     180
cacgggaatg acaatggata aagtgagctg gtacagaaa gccaaactcg ctgagcaggc      240
tgagcgatat gatgatatgg ctgcagccat gaaggcagtc acagaacagg gcatgaact      300 ctccaacgaa gagagaaatc tgctctctgt tgcctacaag aatgtggtag gcgcccgccg     360
ctcttcctgg cgtgtcatct ccagcattga gcagaaaaca gagaggaatg agaagaagca    420
gcagatgggc aaagagtacc gtgagaagat agaggcagaa ctgcaggaca tctgcaatga    480
tgttctggag ctgttggaca atatcttat tcccaatgct acacaaccag aaagtaaggt     540
gttctacttg aaaatgaaag gagattattt taggtatctt tctgaagtgg catctggaga    600
caacaaacaa accactgtgt cgaactccca gcaggcttac caggaagcat tgaaattag     660 taagaaagaa atgcagccta cacacccaat tcgtcttggt ctggcactaa atttctcagt    720 ctttactat gagattctaa actctcctga aaaggcctgt agcctggcaa aacggcatt     780 tgatgaagca attgctgaat ggatacgct gaatgaagag tcttataaag acagcactct    840
gatcatgcag ttacttaggg acaatctcac tctgtggaca tcggaaaacc agggagacga    900
aggagacgct ggggagggag agaactaatg tttctcgtgc tttgtgatct gttcagtgtc    960
actctgtacc ctcaacatat atcccttgtg cgataaaaaa aaaaaaaaaa aaaaaaagag   1020
aatcgtacgt cgactttcga ttttttcacag cctcagccta ggaaaaatgg ttcatgggat   1080

```
aaacagctgg tatttgtatc taaaactcag attggtcaca taaatgccac ggcattccga      1140
agttttgatt ttgattaaca ttgacaggat tactgtgtgt ttaattttt aaaaactgaa       1200 cactgtgatt atggggtttt gtaatttagc agaactctta ctggtagaaa aaatagacct      1260
gaattatgtg taacttttg gaaggtttaa tctgatatca aaataatcat tgaaatacaa       1320
ttccattgta aagttgtaca gaaagttata gagattatat tgtgatgctg gaacttggag      1380
tgagacacac atcatttggc atttgagttg aatggtaatt cacagtaatg ctgccgttgt     1440
tcgggactta aagacacttg acctgttttgg gctgttgcca cttaaaagtt catgaccaca     1500
aatgtccaca gtgtcttcct ctgaggaaac tcgaatcctg aaatgaaat tctttgtggc      1560 agataactgg cttatgacac cttgaaaagt tcaagtgctc atataacaca ccacactgaa     1620 cccccttttcc tacagcaata tgttcactat gttaccaatt tgcaacttgt gcttcaatag     1680
tggaatctac tttcattgtt aacactgagc taaagaaaaa aagccgtgtg ttttatgaat      1740
gaccttatct gttcctgga taataccttt aagaataatg tcctgagtca ggcgtggtgg       1800
tgcgtgcatc tagtcccaac tatttgggag gctgaggcag gaggatcgct tgagcccagg      1860
agtttaaagc tgcagtgccc tgtggttgca cctgtaata actgcactcc agcctgggca      1920
acatagcgag acctcatctc caaaaaagaa aacaaaaac aaaaaagga atgatgttct       1980 gtagagatgg cctttcactt gaggagtact cagttttcag gttcttccta gctcggggct      2040
tttaaatttt gaaatctaaa cattctttcc caccatcctt tttgactgtt gaccttggtt      2100
ttctcttcta agtttctgtc cctctgcttc cttactttt ttccttttg aattctatct        2160 ttatctgtct tttgttcact ttttaatgct atatatgggc agggggtgaga gacattactg     2220 agcaccttgg tgagcaagcc tggctttaaa gattggagaa gagcttctgg caccagaacc      2280
ctgtcttcct ccagttctca acacggtgtt gctcttcagt cataccggaa tctgaatcaa     2340
aaaagtattt ttaaatatcc atgatttctc cctgtattga ggctagccct gatcatgctt     2400
tttgtgcctg tcaccaggtc tcccaagtgc actcatccag gtcagtgctc agatgtgttt     2460
aaggagaccc tatattcagg gaagttgcgt gaacactgca gtggggagaa ttgagaatag      2520
tcaggcctat cagtctcaca gaatcacccc tctacctttg atattccact tagctgtaga     2580
gtccatctgt ttgtccatct gctgaaatga gaaaagaaaa atttatgcac tgatttaaaa     2640
caaaccaaaa aaaagaaaaa aaacaaaaaa aaaaatccct cctttctagc tgaacaaaaa     2700
tgtgcagtta atacttggcg cttgaaaatg cagtagtgaa tgtggaacca agcctgtctg     2760
tatatctggt agctctttc ttgctttgtt ttttcttacc agtattctgc ctaacgtttg      2820
cttctgtgat ggttatattg cctagcaagc acacccgtgg ttgtgaaaat agtatagcaa     2880
aaaagaaaaa tccccggtta ttgatgtact agatttgtgt atgtcttta aacagttcta     2940 gtttcacctt acacagaata atcaggaaaa gtgtaaaaat tcaaaagtga aataaaaatt     3000
ttatcagtta aaaaa                                                      3015
```

<210> SEQ ID NO 9
<211> LENGTH: 3747
<212> TYPE: DNA
<213> ORGANISM: Homo sapiens
<220> FEATURE:
<223> OTHER INFORMATION: 14-3-3 gamma cDNA (NM_012479) 3747 nt

<400> SEQUENCE: 9

```
cagcagccgc agccgcctcg cgcccggtcc cgcggtcgca gctccagccg cctcctccgc      60
```

-continued

```
gcagccgccg cctcagctgc tcgctctgtg ggtcggtcct ctccggcact tgggctccag    120
tcgcgccctc caagcccttc aggccgcccc agtgtcctcc tccttctccg gccagaccca    180
gccccgcgaa gatggtggac cgcgagcaac tggtgcagaa agcccggctg ccgagcagg     240 cggagcgcta cgacgacatg gccgcggcca tgaagaacgt gacagagctg aatgagccac    300
tgtcgaatga ggaacgaaac cttctgtctg tggcctacaa gaacgttgtg ggggcacgcc    360
gctcttcctg gagggtcatc agtagcattg agcagaagac atctgcagac ggcaatgaga    420
agaagattga gatggtccgt gcgtaccggg agaagataga gaaggagttg gaggctgtgt    480
gccaggatgt gctgagcctg ctggataact acctgatcaa gaattgcagc gagacccagt    540
acgagagcaa agtgttctac ctgaagatga aggggacta ctaccgctac ctggctgaag     600
tggccaccgg agagaaaagg gcgacggtgg tggagtcctc cgagaaggcc tacagcgaag    660
cccacgagat cagcaaagag cacatgcagc ccacccaccc catccgatta ggcctggctc    720
ttaactactc cgtcttctac tatgagatcc agaacgcccc agagcaagcg tgccacttgg    780
ccaagaccgc gttcgacgac gccatcgccg agcttgacac cctcaacgag gactcctaca    840
aggactccac gctcatcatg cagctcctcc gcgacaacct cacgctctgg acgagcgacc    900
agcaggacga cgatggcggc gaaggcaaca attaaggccc caggggaact ggcagcgcac    960
gcggatgcta ctactgcagt ctttattttt ttcccatgag ttgggggtcg ggtgggggag    1020 ggaagggag ggatgacctt cccagggaga acccacgac ctgtcctgtc tttgatcgcc       1080
tctttgacat ttttgccaaa ataccactag tggaaagtca ggctagctgt gctggtattg    1140
gaatagcagc ctcacactgg cgtctggact gttctgtaga ttcatgcaag tggagctgtc    1200
tgtctctaat ttaacttatt gctagataat agggttttca gatgaaaaga aaacttaaag    1260
aggaatggcc ctcattcagt aagttctgtg gttccagtaa ggattttat gtacatacgc     1320 tctcgtctct cgtttgggt actttctatc tcatctgtct cggctctgca tgttttccag     1380
ggtgtagcct acagacatgg aacagtgtaa atcccagact gacagactta gaacctgagg    1440
tctcattcat ccttatggtt taggccttgc cagttttccg aagtctctga ttagttgaca    1500
gtattaacac taaattgcag tttacagtat ttctacatta cagccatatg taacatcaag    1560
ccatcgattg tgtactttc ctttgctagt tgtttgggct ttaacatcct tattcagcct     1620
tatccaggtt ggttttgctg ttgatcggtc tcctaggcta aatgagaatg aaagcgactt    1680 caggttttg gttcataggt gctcggcagg tggctgtggg attttttttt ttttggtcc      1740 ttctttcctc ttaacgtaaa tccaccacca aaattattaa tcctcttgag agaaacgtga    1800
aacgccacaa aaatagagaa aattcaggtc tgtatgtcat ggatcgtgtt ggtatttca     1860 gagaacatcc cgcttctgaa gctgctgcag ctccctcctc agggatcaca ctgccgtcac    1920
ccactctgca ctggggcgtt tcctactgcg cctcgtgctg gcggacgcag ctgggtgcag    1980
aagctgtggg gtcggagagg cgtttggaga aggtctgtgg tgcagtgtgt gaaaattcag    2040
gtgctagaag cctactggta gaaaaaccca aaaggaagag ctatatcctt aaccattctg    2100
tccaatttcg ggagccttgt cagtgtgtca gttttttcctc cccgaagaca ctccttcccc    2160
aagtaattgt aggaagataa aaaaactgtt accagataac aaacactgaa ctcctatttg    2220
accagaactt tttcctctcg agatagtttt ttcttttttaa tgaaaaagc ataggaattg     2280 gagattggct tgtctcacgc agccagtgca catttggaat tgacgaaaac aacgttgcta    2340
tttccaccca tttgttttcg gcagccttaa ggccctcatt tcatttcgg gtgaatctgt      2400 ctatctgtga acgtggcccg catgtgcatt cttttttta tatatataaa gtcagtgacg      2460
```

-continued

```
aggaactccc gagacgtgta atgacaccac acttgttttc tttgtttctt tgttttattt      2520
aggcaagaag aggtgtgagt aattgaggaa aaactgacag atgcttttgc taataccaaa      2580
attgagctta caattaggaa ctgagtatgt gtaacaggat acaggtgaca gtgaagatag      2640
aagaaccacg atgaccacag actcaatgtg ctctgtaaca tcgcacagtt tacccagcat      2700
gactttcctt aggaggcccc ctcctcacgc tagagtaaaa gtcccagtta agtgaagcct      2760
accagaagaa ctagtagaag aagctttgcc gcttttgtgc ctctcacagg cgcctaaagt      2820
cattgccatg ggaggaagac gatttggggg gggaggggg gggcagggta ggtgggctt        2880 tccctaattt atcttcatgt ccagtgagca gtgttgcgtt tttccttgta gcatttggaa      2940
atgatttact ggaattacaa aacctatttt tcctttaaat ttcagctttg gctctggctg      3000 cttttttagaa taatgcaaga taaaaatcac acctgagggc tgaaaacgga gagggaatgg    3060
gagacttgat atttaagcag cttgaatggt ttttcttttc tttatttta aagaaatgca      3120 cttgcctatg atactgtctc tccagtgaaa tgattactcc tccattactc tattgataca    3180
atattgtgca tgctagtgtt gtatttctat acagtagctt gaaattgatt aacttatact    3240
gtaggtgtta tgtattccta tgacaaaaaa aattaagtct tcaaattttt taaaggtttt    3300
ttttttttaa tttaattttt cctttttgggg gtaaagtttg ctctaccaaa tagtgattgt    3360
aacaaattga tctgttttgg atgttgctat agtgacatgc agttatatat tttgttttta    3420
aaaggggggg agcaaaagaa acaccagtgt tagcttaatc ttaatgtctg gtgtttgtca    3480
tggtgaaatt ataactatta cagtgttgga gaacaacaaa tatgttctct gaatgagcct    3540
ttgtgctttt tgtcatgtta tgcagtgaac tattttaag gtctaatcag tgattatttt     3600
tccagctccg tgtttctcta aggaattatt tcacacacgg accatcttta gcagtttcct    3660
cagtgatgga atatcatgaa tgtgagtcat tatgtagctg tcgtacattg agcaaataaa    3720
cttacagatc tgaaaaaaaa aaaaaaa                                        3747
```

<210> SEQ ID NO 10
<211> LENGTH: 1810
<212> TYPE: DNA
<213> ORGANISM: Homo sapiens
<220> FEATURE:
<223> OTHER INFORMATION: 14-3-3 epsilon cDNA (NM_006761) 1810 nt

<400> SEQUENCE: 10

```
cggattgagg cgccgccatt tttgctgccc ggacgcggag cgagaggctg agagagtcgg      60
agacactatc cgcttccatc cgtcgcgcag accctgccgg agccgctgcc gctatggatg     120
atcgagagga tctggtgtac caggcgaagc tggccgagca ggctgagcga tacgacgaaa     180
tggtggagtc aatgaagaaa gtagcaggga tggatgtgga gctgacagtt gaagaaagaa    240
acctcctatc tgttgcatat aagaatgtga ttggagctag aagagcctcc tggagaataa    300
tcagcagcat tgaacagaaa gaagaaaaca agggaggaga agacaagcta aaaatgattc    360
gggaatatcg gcaaatggtt gagactgagc taaagttaat ctgttgtgac attctggatg    420
tactggacaa acacctcatt ccagcagcta cactggcga gtccaaggtt ttctattata    480
aaatgaaagg ggactaccac aggtatctgg cagaatttgc cacaggaaac gacaggaagg    540
aggctgcgga gaacagccta gtggcttata agctgctag tgatattgca atgacagaac    600
ttccaccaac gcatccctatt cgcttaggtc ttgctctcaa ttttttccgta ttctactacg   660 aaattcttaa ttcccctgac cgtgcctgca ggttggcaaa agcagctttt gatgatgcaa    720
```

```
ttgcagaact ggatacgctg agtgaagaaa gctataagga ctctacactt atcatgcagt      780
tgttacgtga taatctgaca ctatggactt cagacatgca gggtgacggt gaagagcaga      840
ataaagaagc gctgcaggac gtggaagacg aaaatcagtg agacataagc caacaagaga      900
aaccatctct gaccaccccc tcctccccat cccacccttt ggaaactccc cattgtcact      960
gagaaccacc aaatctgact tttacatttg gtctcagaat ttaggttcct gccctgttgg     1020
tttttttttt ttttttttt aaacagtttt caaaagttct taaaggcaag agtgaatttc      1080
tgtggatttt actggtccca gcttttaggt tctttaagac actaacagga ctacatagag     1140 gcttttcag cattactgtg tcgtctccgt gccagatgtg gcaagatcac cattagcaaa     1200
tggaaattac atttgaaagc cattagactt ataggtgatg caagcatcta agagagaggt     1260
taatcacact atagaggcat aagtggtatc agttttcatt tttctaattg tttaaactgt     1320
gttttatacc agtgtttgca agtaattggg tgttagcttg agatggttaa aggtggtttg     1380
gggagggact tcgttgtaat ggttttgctg taaaaaatgt ttccaactcc gctgaaatgt     1440
tgctgaaaag catggtgctg gtaacagttc aacaatccgt ggctgctcat tcttgcctac     1500
tttactctcc cactgaagca ggttagcgtt gaaggtggta tggaaaagcc tgcatgcctg     1560
ttcaattctt ttgtttcttc tccttccccc tcccctacc tccttcccct cactcctccc     1620
ctccttcgct cgctcaacct cttttgttca gtatgtgtaa cttgaagcta atttgtacta     1680
ctggatatct gactggagcc acagatacag aatctgtatt gttcttactg aaacacagca     1740
tggaattaac attaaactta aataaaacaa acctaaatta aaaaaaaaa aaaaaaaaa      1800 aaaaaaaaaa                                                            1810

<210> SEQ ID NO 11
<211> LENGTH: 1807
<212> TYPE: DNA
<213> ORGANISM: Homo sapiens
<220> FEATURE:
<223> OTHER INFORMATION: 14-3-3 eta cDNA (NM_003405) 1807 nt

<400> SEQUENCE: 11
gcggccgcgt ctcctccctc ggcgttgtcc gcggcgcgag ccacagcgcg cggggcgagc       60
cagcgagagg gcgcgagcgg cggcgctgcc tgcagcctgc agcctgcagc ctccggccgg      120
ccggcgagcc agtgcgcgtg cgcggcggcg gcctccgcag cgaccgggga gcggactgac      180
cggcgggagg gctagcgagc cagcggtgtg aggcgcgagg cgaggccgag ccgcgagcga      240
catgggggac cgggagcagc tgctgcagcg ggcgcggctg gccgagcagg cggagcgcta      300
cgacgacatg gcctccgcta tgaaggcggt gacagagctg aatgaacctc tctccaatga      360
agatcgaaat ctcctctctg tggcctacaa gaatgtggtt ggtgccaggc gatcttcctg      420
gagggtcatt agcagcattg agcagaaaac catggctgat ggaaacgaaa agaaattgga      480 gaaagtaaa gcttaccggg agaagattga gaaggagctg gagacagttt gcaatgatgt      540
cctgtctctg cttgacaagt tcctgatcaa gaactgcaat gatttccagt atgagagcaa      600
ggtgttttac ctgaaaatga agggtgatta ctaccgctac ttagcagagg tcgcttctgg      660
ggagaagaaa aacagtgtgg tcgaagcttc tgaagctgcc tacaaggaag cctttgaaat      720
cagcaaagag cagatgcaac ccacgcatcc catccggctg ggcctggccc tcaacttctc      780
cgtgttctac tatgagatcc agaatgcacc tgagcaagcc tgcctcttag ccaaacaagc      840
cttcgatgat gccatagctg agctggacac actaaacgag gattcctata aggactccac      900
gctgatcatg cagttgctgc gagacaacct caccctctgg acgagcgacc agcaggatga      960
```

```
agaagcagga gaaggcaact gaagatcctt caggtcccct ggcccttcct tcacccacca    1020
cccccatcat caccgattct tccttgccac aatcactaaa tatctagtgc taaacctatc    1080
tgtattggca gcacagctac tcagatctgc actcctgtct cttgggaagc agtttcagat    1140
aaatcatggg cattgctgga ctgatggttg ctttgagccc acaggagctc ccttttttgaa   1200 ttgtgtggag aagtgtgttc tgatgaggca ttttactatg cctgttgatc tatgggaaat    1260
ctaggcgaaa gtaatgggga agattagaaa gaattagcca accaggctac agttgatatt    1320
taaaagatcc atttaaaaca agctgatagt gtttcgttaa gcagtacatc ttgtgcatgc    1380
aaaaatgaat tcacccctcc cacctctttc ttcaattaat ggaaaactgt taagggaagc    1440
tgatacagag agacaacttg ctcctttcca tcagctttat aataaactgt ttaacgtgag    1500
gtttcagtag ctccttggtt ttgcctcttt aaattatgac gtgcacaaac cttcttttca    1560
atgcaatgca tctgaaagtt ttgatacttg taacttttttt tttttttttgg ttgcaattgt   1620 ttaagaatca tggatttatt ttttgtaact ctttggctat tgtccttgtg tatcctgaca    1680
gcgccatgtg tgtcagccca tgtcaatcaa gatgggtgat tatgaaatgc cagacttcta    1740
aaataaatgt tttggaattc aatgggtaaa taaatgctgc tttggggata ttaaaaaaaa    1800
aaaaaaa                                                               1807

<210> SEQ ID NO 12
<211> LENGTH: 2166
<212> TYPE: DNA
<213> ORGANISM: Homo sapiens
<220> FEATURE:
<223> OTHER INFORMATION: 14-3-3 tau cDNA (NM_006826) 2166 nt

<400> SEQUENCE: 12
gtggtgggac tcgcgtcgcg gccgcggaga cgtgaagctc tcgaggctcc tcccgctgcg      60
ggtcggcgct cgccctcgct ctcctcgccc tccgccccgg ccccggcccc gcgcccgcca     120
tggagaagac tgagctgatc cagaaggcca agctggccga gcaggccgag cgctacgacg     180
acatggccac ctgcatgaag gcagtgaccg agcagggcgc cgagctgtcc aacgaggagc     240
gcaacctgct ctccgtggcc tacaagaacg tggtcggggg ccgcaggtcc gcctggaggg     300
tcatctctag catcgagcag aagaccgaca cctccgacaa gaagttgcag ctgattaagg     360
actatcggga gaaagtggag tccgagctga gatccatctg caccacggtg ctggaattgt     420
tggataaata tttaatagcc aatgcaacta atccagagag taaggtcttc tatctgaaaa     480
tgaagggtga ttacttccgg taccttgctg aagttgcgtg tggtgatgat cgaaaacaaa     540
cgatagataa ttcccaagga gcttaccaag aggcatttga tataagcaag aaagagatgc     600
aacccacaca cccaatccgc ctggggcttg ctcttaactt ttctgtattt tactatgaga     660
ttcttaataa cccagagctt gcctgcacgc tggctaaaac ggcttttgat gaggccattg     720
ctgaacttga tacactgaat gaagactcat acaaagacag cacccctcatc atgcagttgc    780 ttagagacaa cctaacactt tggacatcag acagtgcagg agaagaatgt gatgcggcag     840
aaggggctga aaactaaatc catacagggt gtcatccttc tttccttcaa gaaaccttt     900 tacacatctc cattccttat tccacttgga tttcctatag caaagaaacc cattcatgtg     960
tatgaaatca actgtttata gtcttttcac actgcagctt tgggaaaact tcattccttg    1020
atttgtgttt gtcttggcct tcctggtgtg cagtactgct gtagaaaagt attaatagct    1080
tcatttcata taaacataag taactcccaa acacttatgt agaggactaa aaatgtatct    1140
```

-continued

| | |
|---|---|
| ggtatttaag taatctgaac cagttctgca agtgactgtg ttttgtatta ctgtgaaaat | 1200 |
| aagaaaatgt agttaattac aatttaaaga gtattccaca taacttctta atttctacat | 1260 |
| tccctccctt actcttcggg ggtttccttt cagtaagcaa cttttccatg ctcttaatgt | 1320 |
| attccttttt agtaggaatc cggaagtatt agattgaatg gaaaagcact tgccatctct | 1380 |
| gtctagggt cacaaattga atggctcct gtatcacata cggaggtctt gtgtatctgt | 1440 |
| ggcaacaggg agtttcctta ttcactcttt atttgctgct gtttaagttg ccaacctccc | 1500 |
| ctcccaataa aaattcactt acacctcctg cctttgtagt tctggtattc actttactat | 1560 |
| gtgatagaag tagcatgttg ctgccagaat acaagcattg cttttggcaa attaaagtgc | 1620 |
| atgtcatttc ttaatacact agaaagggga aataaattaa agtacacaag tccaagtcta | 1680 |
| aaactttagt acttttccat gcagatttgt gcacatgtga gagggtgtcc agtttgtcta | 1740 |
| gtgattgtta tttagagagt tggaccacta ttgtgtgttg ctaatcattg actgtagtcc | 1800 |
| caaaaagcc ttgtgaaaat gttatgccct atgtaacagc agagtaacat aaaataaaag | 1860 |
| tacattttat aaaccattta ctatggcttt gtaacaattg catacccata ttttaaggga | 1920 |
| caggtgaatt tactactttc taaagtttat tgatacttcc cttttatgta aaatgtagta | 1980 |
| gtgataccta tatttccaca ttgtgcattg tgacacactt gtctagggat gcctggaagt | 2040 |
| gtataaaatt ggactgcatt tcttagagtg ttttactata gatcagtctc atgggccatc | 2100 |
| tcttcctcag atgtaaatga tatctggtta agtgttatat ggaataaagt ggacatttta | 2160 |
| aaacta | 2166 |

<210> SEQ ID NO 13
<211> LENGTH: 1329
<212> TYPE: DNA
<213> ORGANISM: Homo sapiens
<220> FEATURE:
<223> OTHER INFORMATION: 14-3-3 sigma cDNA (NM_006142) 1336 nt

<400> SEQUENCE: 13

| | |
|---|---|
| gagagacaca gagtccggca ttggtcccag gcagcagtta gcccgccgcc cgcctgtgtg | 60 |
| tccccagagc catggagaga gccagtctga tccagaaggc caagctggca gagcaggccg | 120 |
| aacgctatga ggacatggca gccttcatga aaggcgccgt ggagaagggc gaggagctct | 180 |
| cctgcgaaga gcgaaacctg ctctcagtag cctataagaa cgtggtgggc ggccagaggg | 240 |
| ctgcctggag ggtgctgtcc agtattgagc agaaaagcaa cgaggagggc tcggaggaga | 300 |
| aggggcccga ggtgcgtgag taccgggaga aggtggagac tgagctccag ggcgtgtgcg | 360 |
| acaccgtgct gggcctgctg gacagccacc tcatcaagga ggccggggac gccgagagcc | 420 |
| gggtcttcta cctgaagatg aagggtgact actaccgcta cctggccgag gtggccaccg | 480 |
| gtgacgacaa gaagcgcatc attgactcag cccggtcagc ctaccaggag gccatggaca | 540 |
| tcagcaagaa ggagatgccg cccaccaacc ccatccgcct gggcctggcc ctgaactttt | 600 |
| ccgtcttcca ctacgagatc gccaacagcc ccgaggagca catctctctg gccaagacca | 660 |
| ctttcgacga ggccatggct gatctgcaca ccctcagcga ggactcctac aaagacagca | 720 |
| ccctcatcat gcagctgctg cgagacaacc tgacactgtg gacggccgac aacgccgggg | 780 |
| aagaggggg cgaggctccc caggagcccc agagctgagt gttgcccgcc accgccccgc | 840 |
| cctgccccct ccagtccccc accctgccga ggactagt atgggtggg aggccccacc | 900 |
| cttctccccct aggcgctgtt cttgctccaa agggctccgt ggagggac tggcagagct | 960 |
| gaggccacct ggggctgggg atcccactct tcttgcagct gttgagcgca cctaaccact | 1020 |

```
ggtcatgccc caccccctgc tctccgcacc cgcttcctcc cgaccccagg accaggctac    1080
ttctcccctc ctcttgcctc cctcctgccc ctgctgcctc tgatcgtagg aattgaggag    1140
tgtcccgcct tgtggctgag aactggacag tggcaggggc tggagatggg tgtgtgtgtg    1200
tgtgtgtgtg tgtgtgtgtg tgtgcgcgcg cgccagtgca agaccgagat tgagggaaag    1260
catgtctgct gggtgtgacc atgtttcctc tcaataaagt tcccctgtga cactcaaaaa    1320
aaaaaaaaa                                                            1329
```

<210> SEQ ID NO 14
<211> LENGTH: 2876
<212> TYPE: DNA
<213> ORGANISM: Homo sapiens
<220> FEATURE:
<223> OTHER INFORMATION: 14-3-3 zeta cDNA (NM_145690) 2876 nt

<400> SEQUENCE: 14

```
gcctgtgagc agcgagatcc agggacagag tctcagcctc gccgctgctg ccgccgccgc      60
cgcccagaga ctgctgagcc cgtccgtccg ccgccaccac ccactccgga cacagaacat     120
ccagtcatgg ataaaaatga gctggttcag aaggccaaac tggccgagca ggctgagcga     180
tatgatgaca tggcagcctg catgaagtct gtaactgagc aaggagctga attatccaat     240
gaggaggagg atcttctctc agttgcttat aaaaatgttg taggagcccg taggtcatct     300
tggagggtcg tctcaagtat tgaacaaaag acggaaggtg ctgagaaaaa acagcagatg     360
gctcgagaat acagagagaa aattgagacg gagctaagag atatctgcaa tgatgtactg     420
tctcttttgg aaaagttctt gatccccaat gcttcacaag cagagagcaa agtcttctat     480
ttgaaaatga aggagatta ctaccgttac ttggctgagg ttgccgctgg tgatgacaag     540
aaagggattg tcgatcagtc acaacaagca taccaagaag cttttgaaat cagcaaaaag     600
gaaatgcaac caacacatcc tatcagactg ggtctggccc ttaacttctc tgtgttctat     660
tatgagattc tgaactcccc agagaaagcc tgctctcttg caaagacagc ttttgatgaa     720
gccattgctg aacttgatac attaagtgaa gagtcataca aagacagcac gctaataatg     780
caattactga gagacaactt gacattgtgg acatcggata cccaaggaga cgaagctgaa     840
gcaggagaag aggggaaaa ttaaccggcc ttccaacttt tgtctgcctc attctaaaat     900
ttacacagta gaccatttgt catccatgct gtcccacaaa tagttttttg tttacgattt     960
atgacaggtt tatgttactt ctatttgaat ttctatattt cccatgtggt ttttatgttt    1020
aatattaggg gagtagagcc agttaacatt tagggagtta tctgttttca tcttgaggtg    1080
gccaatatgg ggatgtggaa tttttataca agttataagt gtttggcata gtacttttgg    1140
tacattgtgc cttcaaaagg gccagtgtaa aactgcttcc atgtctaagc aaagaaaact    1200
gcctacatac tggtttgtcc tggcggggaa taaaagggat cattggttcc agtcacaggt    1260
gtagtaattg tgggtacttt aaggtttgga gcacttacaa ggctgtggta gaatcatacc    1320
ccatggatac cacatattaa accatgtata tctgtggaat actcaatgtg tacacctttg    1380
actacagctg cagaagtgtt cctttagaca aagttgtgac ccatttact ctggataagg    1440 gcagaaacgg ttcacattcc attatttgta agttacctg ctgttagctt tcattatttt    1500
tgctacactc atttatttg tatttaaatg ttttaggcaa cctaagaaca aatgtaaaag    1560
taaagatgca ggaaaatga attgcttggt attcattact tcatgtatat caagcacagc    1620
agtaaaacaa aaacccatgt atttaacttt tttttaggat ttttgctttt tgtgattttt    1680
```

```
ttttttttttt ttgatacttg cctaacatgc atgtgctgta aaatagtta acagggaaat    1740 aacttgagat gatggctagc tttgtttaat gtcttatgaa attttcatga acaatccaag    1800
cataattgtt aagaacacgt gtattaaatt catgtaagtg gaataaaagt tttatgaatg    1860
gacttttcaa ctactttctc tacagctttt catgtaaatt agtcttggtt ctgaaacttc    1920
tctaaaggaa attgtacatt ttttgaaatt tattccttat tccctcttgg cagctaatgg    1980
gctcttacca agtttaaaca caaaatttat cataacaaaa atactactaa tataactact    2040
gtttccatgt cccatgatcc cctctcttcc tccccaccct gaaaaaaatg agttcctatt    2100
ttttctggga gaggggggga ttgattagaa aaaaatgtag tgtgttccat ttaaaatttt    2160
ggcatatggc attttctaac ttaggaagcc acaatgttct tggcccatca tgacattggg    2220
tagcattaac tgtaagtttt gtgcttccaa atcactttt ggtttttaag aatttcttga     2280
tactcttata gcctgccttc aattttgatc ctttattctt tctatttgtc aggtgcacaa    2340
gattaccttc ctgttttagc cttctgtctt gtcaccaacc attcttactt ggtggccatg    2400
tacttggaaa aaggccgcat gatctttctg gctccactca gtgtctaagg caccctgctt    2460
cctttgcttg catcccacag actatttccc tcatcctatt tactgcagca aatctctcct    2520
tagttgatga gactgtgttt atctcccttt aaaaccctac ctatcctgaa tggtctgtca    2580
ttgtctgcct ttaaaatcct tcctctttct tcctcctcta ttctctaaat aatgatgggg    2640
ctaagttata cccaaagctc actttacaaa atatttcctc agtactttgc agaaaacacc    2700
aaacaaaaat gccattttaa aaaggtgta ttttttcttt tagaatgtaa gctcctcaag     2760
agcagggaca atgttttctg tatgttctat tgtgcctagt acactgtaaa tgctcaataa    2820
atattgatga tgggaggcag tgagtcttga tgataagggt gagaaactga aatccc        2876
```

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer used for PCR amplification of the 14-3-3 eta cDNA

<400> SEQUENCE: 15
gcgaattcct gcagcgggcg cggctggccg a                                    31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer used for PCR amplification of the 14-3-3 eta cDNA

<400> SEQUENCE: 16
gctcgagcct gaaggatctt cagttgcctt c                                    31

DISSOLVED PROTEIN ARTHRITIS MARKERS

CROSS-REFERENCE

This application a continuation of U.S. patent application Ser. No. 12/637,730, filed Dec. 14, 2009, which is a continuation of U.S. patent application Ser. No. 12/300,118, filed Nov. 6, 2008, which is a National Phase Entry of PCT Application No. PCT/CA2007/000817, filed May 9, 2007, which claims the benefit of U.S. Provisional Application No. 60/798,712, filed May 9, 2006, each of which is incorporated herein by reference in their entirety.

SEQUENCE LISTING

The instant application contains a Sequence Listing which has been submitted in ASCII format via EFS-Web and is hereby incorporated by reference in its entirety. Said ASCII copy was created on Oct. 13, 2017, is named 177000-seq-list.txt and is 40,524 bytes in size.

FIELD OF THE INVENTION

The invention relates to assays for selected protein isoforms that are diagnostic biomarkers for arthritis when those proteins are found in extracellular fluids.

BACKGROUND OF THE INVENTION

Arthritis or arthralgia generally refers to inflammatory disorders of the joints of the body, and is usually accompanied by pain, swelling and stiffness. Arthritis may result from any of several causes including infection, trauma, degenerative disorders, metabolic disorders or disturbances or other unknown etiologies. Arthritis may be more specifically described as, for example, rheumatoid arthritis, osteoarthritis, bacterial or infectious arthritis. Arthritis may further accompany other identified disorders, including gout, ankylosing spondylitis, inflammatory bowel disease or psoriasis.

In normal joints, a small amount of synovial fluid (SF) lubricates cartilage and the synovium, and acts as a reservoir for solutes and a few resting mononuclear and synovial cells (3). During chronic inflammation, SF volume and the concentration of immune cells and soluble proteins increase (4).

For some forms of arthritis, such as rheumatoid arthritis (RA), the specific cause may not be known. RA is regarded as a "multifactorial threshold model", in which many genetic and environmental influences must act on the same person in order for the disease to manifest (1). As a specific target is lacking, current therapies are primarily aimed at suppression of the inflammatory response (2). A hallmark of RA is synovial hyperplasia, characterized by fibroblast-like synoviocyte (FLS) proliferation and inflammatory cell infiltration into the subintima, or outer layer of the synovium (5). The FLS, which comprise about two-thirds of the synovium population, have a well-defined secretory system (5) and secrete large amounts of destructive matrix metalloproteases (MMPs) in RA (6), specifically MMP-1, 3, 8, 9, 10, 11 and 13 (7-11). Numerous researchers have shown that MMP-1 and MMP-3 play important roles in RA (12) and that the collagenase (MMP-1) is the most abundant (6). Both MMP-1 and MMP-3 are biomarkers that have been shown to have predictive validity for structural damage in RA. Local expression of MMPs in arthritis, especially MMP-1, is particularly prominent in the joint pannus adjacent to the site of cartilage and bone destruction (13). The collagenases, particularly MMP-1, cleave native collagen molecules at neutral pH, rendering the collagen susceptible to further enzymatic degradation (14).

Known factors that activate FLS to produce MMP-1 include pro-inflammatory cytokines such as interleukin-1 (IL-1) and tumour necrosis factor alpha (TNF-alpha), and both are involved in RA (15). IL-1alpha and TNF-alpha are capable of stimulating the production of other MMPs and stromelysins in synovial fibroblasts and chondrocytes in vitro (16). The interactions of FLS with TNF-alpha or IL-1 alpha from activated T cells induces expression of MMP-1 (17). T-cells can also activate FLS to produce an array of inflammatory mediators (18). This cyclical feedback loop between FLS and T cells and their respective cytokines lead to activation and proliferation of T cells and favours the persistent inflammation observed in RA (19-21). It has been suggested that therapeutic anti-TNF alpha antibodies neutralize TNF alpha and block the T cell activation that leads to this persistent state (22).

14-3-3 proteins are a family of dimeric proteins involved in a range of functions (23-24). There are seven mammalian 14-3-3 isoforms: beta (β), gamma (γ), epsilon (ε), eta (η), sigma (σ), tau (τ) and zeta (ζ). Since the discovery of the first 14-3-3 protein in 1967 (26), the members of the 14-3-3 protein family have been repeatedly re-discovered based on their new biological activities, primarily in signal transduction pathways. They have been identified as activators of tryptophan and tyrosine hydroxylase (27-28) and PKC inhibitors (29). Subsequent studies identified the 14-3-3 proteins as molecules that interact with PKCs, Raf family members and now more than 200 other intracellular proteins with critical biological functions (30-31) including cellular response to DNA damage and cell cycle regulation (32-34).

SUMMARY OF THE INVENTION

The invention is based in part on the surprising discovery that particular isoforms of the 14-3-3 protein, 14-3-3 eta and gamma, are present at increased levels in the serum and synovial fluid of arthritis patients, compared to normal patients.

In accordance with one aspect of the invention, there is provided a method for predicting responsiveness of a subject to a therapeutic regimen, the subject having, or suspected of having arthritis, the method comprising determining a presence, absence, amount or relative levels of a protein 14-3-3 eta or gamma in a sample, wherein the presence, absence, amount or relative level of the isoform is indicative of a sensitivity of the subject's arthritis to the therapeutic regimen.

In accordance with another aspect of the invention, there is provided a kit for detecting a 14-3-3 eta or gamma protein in a patient sample, such as a sample of sera or synovial fluid from a patient having, or at risk of having, an arthritis. The kit may comprise at least one antibody specific for detecting at least one of these isoforms of the 14-3-3 protein. The kit may further comprise at least one antibody specific for detecting at least one matrix metalloproteinase.

In accordance with another aspect of the invention, there is provided a method for selecting a group of subjects for determining the efficacy of a therapeutic regimen known or suspected of being useful for the treatment of arthritis, the method comprising detecting a presence, absence, amount or relative levels of a 14-3-3 eta or gamma protein in a patient sera or synovial fluid sample, wherein said presence, absence, amount or relative level of one or more of these isoforms of the 14-3-3 protein in that fluid is indicative of a sensitivity of the subject's arthritis to the therapeutic regimen.

In accordance with another aspect of the invention, there is provided a method of treating arthritis in a mammalian subject in need thereof, the method comprising administering to the subject a therapeutic regimen, wherein the presence, absence, amount or relative level of a 14-3-3 eta or gamma protein isoform in sera or synovial fluid from that subject is indicative of sensitivity to the therapeutic regimen.

In accordance with another aspect of the invention, there is provided a method of treating arthritis in a mammalian subject in need thereof, the method comprising: selecting a subject having a presence, absence, amount or relative level of 14-3-3 eta or gamma protein in sera or synovial fluid that is indicative of sensitivity to a therapeutic regimen; and administering to the subject the therapeutic regimen.

In accordance with another aspect of the invention, there is provided a method of identifying a mammalian subject with an increased sensitivity to a therapeutic regimen for treating arthritis, comprising the step of screening a population of subjects for the presence, absence, amount or relative level of 14-3-3 eta or gamma protein in sera or synovial fluid, and identifying subjects sensitive to the therapeutic regimen based at least in part on the presence, absence, amount or relative level of the protein in the fluid.

In selected embodiments, the invention may involve assays for other arthritis markers in the sera or synovial fluids of subjects, in conjunction with assays for the presence, absence, amount or relative level of 14-3-3 eta or gamma proteins. For example, assays of the invention may additionally involve determining the presence, absence, amount or relative levels of one or more matrix metalloproteinases, such as MMP-1 or MMP-3, in sera or synovial fluid samples.

BRIEF DESCRIPTION OF THE DRAWINGS

In drawings which illustrate embodiments of the invention.

Figure 1:
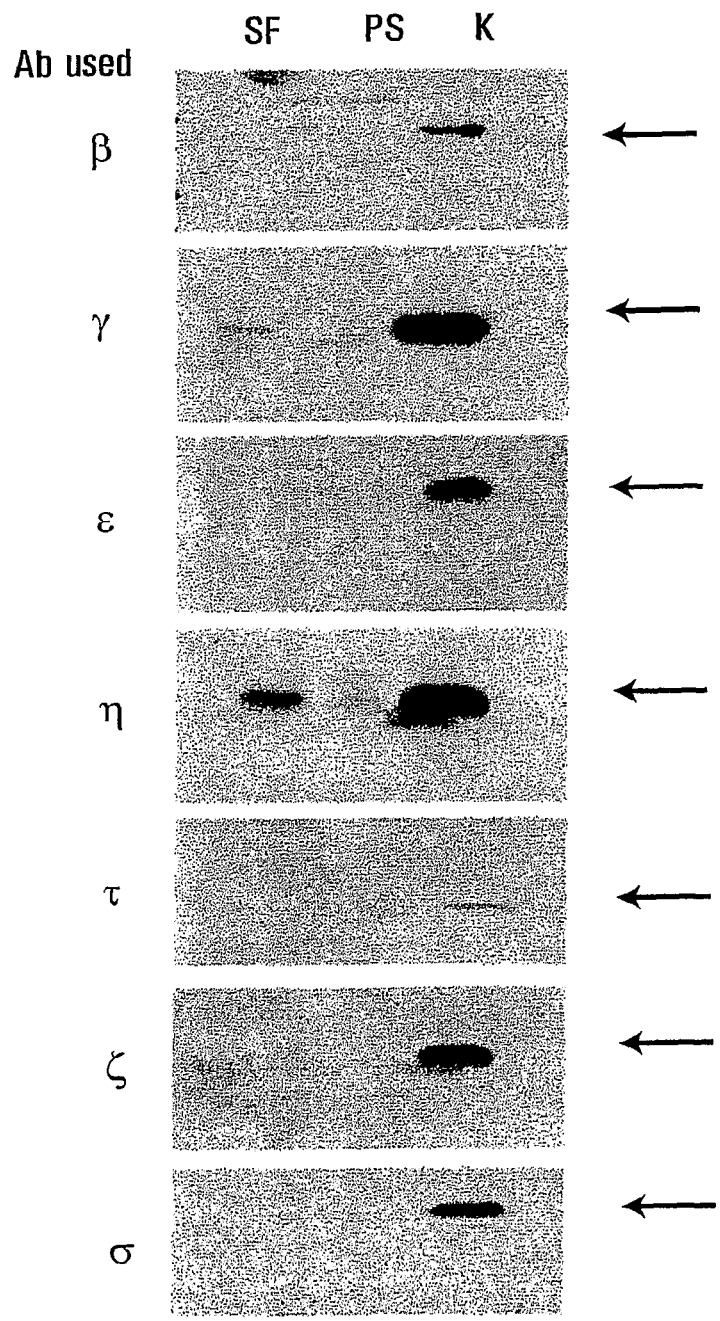
FIG. 1

Detection of various isoforms of 14-3-3 in the synovial fluid (SF) and serum (PS) of arthritic patients by western blot. Keratinocyte lysates (K) was used as a positive control.

FIG. 2

Detection of 14-3-3η in the synovial fluid of 17 arthritic patients. Synovial fluid samples (2 μl/lane) were taken from 17 RA patients who had active synovitis and analyzed by western blot, using an isoform-specific antibody for the 14-3-3 η isoform. Keratinocyte lysate (K) was used as a positive control. Levels of 14-3-3 η vary in the patient population surveyed, but is reliably detected in all synovial fluid samples.

FIG. 3

14-3-3η, MMP-1 and MMP-3 expression in patient sera and synovial fluid. 12 patients' matched synovial fluid and serum samples examined by western blot. Keratinocyte cell lysate (K) was used as a positive control. SF: synovial fluid; PS: patient serum; MMP-1: matrix metalloproteinase 1; MMP-3: matrix metalloproteinase 3.

FIG. 4

Detection and comparison of the levels of 14-3-3η and γ in 9 matched patient serum and synovial fluid samples. Patients' synovial fluid or serum (2 μl/lane) was analyzed by western blot using anti 14-3-3η or γ antibody. Keratinocyte cell lysate (K) was used as a positive control. SF, synovial fluid; PS, patient serum.

FIG. 5

Levels of 14-3-3η in matched patient serum and synovial fluid samples were quantified by densitometry and depicted in lower panel. Solid bars show the level of 14-3-3 η in serum normalized to a synovial fluid sample from the same patient (open bars).

FIG. 6A-B

Detection of 14-3-3 η, γ, MMP-1 and MMP-3 in different volumes of normal and patients sera.

A) Pooled samples of 12 normal or patient sera were prepared and a range of volumes (0.1-2.0 μl/lane) were analyzed by western blot, using specific antibodies for 14-3-3η, γ, MMP-1 or MMP-3. 2 μl of a pooled of synovial fluid (SF) from affected patients was included as a positive control. B) Recombinant 14-3-3 η isoform (0.01-2.0 μg/lane) was analyzed by western blot in parallel with 2 μl of normal (NS) or patient serum (PS).

FIG. 7

Illustrates detection of 14-3-3 η before and after anti-TNF therapy: Levels of 14-3-3 eta protein in 4 ml of serum samples from RA patients before (U) and after anti-TNF-a (T) Treatment. N=negative control which is 4 ml of a pooled serum sample prepared from 12 serum samples taken from 12 healthy individuals. P=positive control which is 4 mg of keratinocyte cell lysate total protein.

DETAILED DESCRIPTION

A "Disease Activity Score" (DAS) refers to a measure of the activity or state of rheumatoid arthritis in a patient. DAS is one of several standards or scores used in clinical practice. A calculation of a DAS may include the following parameters: Number of joints tender to the touch (TEN), number of swollen joints (SW), erythrocyte sedimentation rate (ESR) and patient assessment of disease activity (VAS). Alternatively, a DAS may include C-reactive protein marker assessment (CRP) (Skogh T et al 2003. Ann Rheum Dis 62:681-682).

A patient or test subject, as used herein, includes a human patient undergoing, or about to undergo, treatment for arthritis. A test subject includes non-human mammals undergoing, or about to undergo, treatment for arthritis. In the case of a test subject, the arthritis may be deliberately induced or implanted, or may develop spontaneously. The patient or test subject may have been previously diagnosed using methods described herein, for example, or other diagnostic methods known in the art, or may be selected as part of general population (a 'control' patient or 'control' test subject). Patients and test subjects, whether control or not, may be generally referred to as a subject. Patients may be selected or differentiated on the basis of disease severity, gender, age, or suitability for a particular treatment or assay method.

As used herein, an 'isoform' refers to any two or more of functionally similar proteins that have a similar but not identical amino acid sequence and are either encoded by different genes or by RNA transcripts from the same gene which have had different exons removed.

It will be appreciated by a person of skill in the art that the numerical designations of the positions of nucleotides or amino acids within a sequence are relative to the specific sequence. Also, the same positions may be assigned different numerical designations depending on the way in which the sequence is numbered and the sequence chosen. Furthermore, sequence variations such as insertions or deletions, may change the relative position and subsequently the numerical designations of particular nucleotides or amino acids at or around a particular site.

The terms 'peptide', 'polypeptide' and protein' may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid.

The term 'antibody' as used herein includes polyclonal and monoclonal antibodies, chimeric, single chain, or humanized antibodies, as well as Fab or $F(ab)^2$ fragments, including the products of an Fab or other immunoglobulin expression library. Methods of making such antibodies or fragments are known in the art and may be found in, for example HARLOW, E and LANE D. Antibodies: A Laboratory Manual. 1988. Cold Spring Harbor Laboratory Press. Selection or identification of specific peptides for use as epitopes for production of antibodies that differentiate between proteins, or isoforms of proteins may be made using sequence comparisons—one of skill in the art will be able to identify suitable peptide or protein sequences that may be useful for producing antibodies with the desired selectivities. Examples of sequences that may be useful to one of skill may include SEQ ID NOs: 1-7.

As used herein, 'arthritis' or 'arthralgia' refer to an inflammatory disorder of the joints of the body. Pain, swelling, stiffness and difficulty of movement are frequently associated with arthritis diseases. Arthritis may result from any of several causes including infection, trauma, degenerative disorders, metabolic disorders or disturbances or other unknown etiologies. Arthritis may be more specifically described as, for example, rheumatoid arthritis, osteoarthritis, bacterial or infectious arthritis. Arthritis may further accompany other identified disorders, including gout, ankylosing spondylitis, inflammatory bowel disease or psoriasis.

14-3-3 proteins, particularly the eta and gamma isoforms, may be readily detected in synovial fluid or serum of patients affected with arthritis, for example rheumatoid arthritis. In one embodiment of the invention, detection of these signal transduction proteins in the site of inflammation may have application in early or more simplified diagnosis of arthritis, or differentiation between the various types of arthritis in a patient. Alternatively, the presence or relative levels of isoforms of 14-3-3 proteins may be a prognostic indicator of early-stage arthritis, before it progresses to a debilitating form. An advantage of early prognosis or diagnosis is earlier implementation of a treatment regimen. Alternatively, the presence or relative levels of isoforms of 14-3-3 in a patient sample may be useful to determine patient suitability for a particular treatment regimen.

Treatment regimens for various types of arthritis are known in the art. Therapeutic approaches to arthritis may for example be generally characterised as disease modifying therapy for arthritis, or remittive therapies. For example, a patient diagnosed with rheumatoid arthritis may be prescribed non-steroidal anti-inflammatory medications (NSAIDs) initially, to ease the discomfort and reduce the inflammation. Other treatment regimens may include, for example cyclooxygenase 2 specific inhibitors (CSIs), glucocorticoids, disease-modifying anti-rheumatic drugs (DMARDs), anti-TNF alpha neutralizing agents or immunosuppressive or cytotoxic drugs. Details on dosage or examples of particular drugs will be known to those of skill in the art, and may be found in, for example Harrison's Principles of Internal Medicine $15^{th}$ ed. BRAUNWALD et al eds. McGraw-Hill or "The Pharmacological basis of therapeutics", $10^{th}$ edition. HARDMAN HG., LIMBIRD LE. editors. McGraw-Hill, New York, and in "Clinical Oncology", $3^{rd}$ edition. Churchill Livingstone/Elsevier Press, 2004. ABELOFF, M D. editor.

In another embodiment of the invention, the presence or relative levels of 14-3-3 eta or gamma proteins may correlate with the presence or relative levels of other proteins in the patient sample, for example matrix metalloproteinases (MMPs), such as MMP-1 or MMP-3. MMPs are zinc-binding endopeptidases that degrade components of the extracellular matrix. MMPs have different substrate specificities and are encoded by different genes. At least 25 different MMPs have been identified. Detection of 14-3-3 eta or gamma proteins in combination with at least one MMP in a patient sample may have application in early or more simplified diagnosis of arthritis, or differentiation between the various types of arthritis in a patient. Alternatively, the presence or relative levels of eta or gamma isoforms of 14-3-3 proteins in combination with at least one MMP in a patient sample may be a prognostic indicator of early-stage arthritis, before the arthritis progresses to a debilitating form. An advantage of early prognosis or diagnosis may include earlier implementation of a treatment regimen. Alternatively, the presence or relative levels of eta or gamma isoforms of 14-3-3 in combination with at least one MMP in a patient sample may be useful to determine patient suitability for a particular treatment regimen.

In another embodiment of the invention, a kit for detecting the presence of 14-3-3 eta or gamma proteins or particular MMPs in a patient sample, the kit being suitable for use in providing a diagnostic or prognostic result suitable for diagnosing or differentiating various types of arthritis. A kit may include, for example, antibodies specific for eta or gamma isoforms of 14-3-3 proteins. Such a kit may further include antibodies specific for particular MMPs. The kit may further include other reagents necessary for the detection of 14-3-3 eta or gamma or MMPs immunologically, such as labelled secondary antibodies, chromogenic or fluorogenic reagents, polymerization agents and/or instructions for using the kit for diagnostic or prognostic purposes.

General Methods

Once a subject is identified as being at risk for developing or having arthritis, information useful for assessing the disease state of the diagnosed arthritis, response to a therapeutic treatment regimen for arthritis, or prognosis of arthritis, or the type of arthritis may be obtained from the patient or test subject. Various methods for obtaining biological samples from a subject that contain protein or peptides that may be useful as biomarkers are known in the art. For example, tissue samples may be obtained by curettage, needle aspiration biopsy or needle (core) biopsy, incisional biopsy for sampling a tumor, or excisional biopsy, which may entail total removal of the tissue of interest. Alternatively, other bodily samples that contain genetic material, such as synovial fluid, hair, sputum, urine, stool, semen, plasma, serum or blood may be collected using methods known in the art.

The presence of specific proteins or peptides in a biological sample, or the relative levels of specific proteins or peptides in a biological sample may be detected by any of several methods known in the art. Examples of such methods include mass spectroscopy, immunological-based techniques such as western blotting, ELISA, immunohistochemistry, FACS, surface plasmon resonance or chromatography. Methods for these and other techniques may be found in, for example AUSUBEL et al., Current Protocols in Molecular Biology, John Wiley & Sons, New York, N.Y., 1998: ABELOFF, Clinical Oncology, $3^{rd}$ edition. Churchill Livingstone/Elsevier Press, 2004; HARLOW, E and LANE D. Antibodies: A Laboratory Manual. 1988. Cold Spring Harbor Laboratory Press; SAMBROOK J and RUSSELL D W. Molecular cloning: A Laboratory Manual 2001 Cold Spring Harbor Laboratory Press; Harrison's Principles of Internal Medicine $15^{th}$ ed. BRAUNWALD et al eds. McGraw-Hill. 14-3-3 detection methods are described for example in WO 99/46401, US 2005/9094, WO 97/38315 and WO 97/33601, all of which are incorporated herein be reference.

Western Blotting

Synovial fluid or serum (2 µl of each) was subjected to SDS-PAGE analysis with 12% (wt/vol) acrylamide gel, and electrotransferred onto PVDF membranes (Millipore Corporation). Non-specific proteins on membranes were blocked in 5% skim milk powder in PBS-0.1% Tween-20 overnight. Immunoblotting was performed using 2 µg/ml of 7 isoforms specific rabbit anti-human 14-3-3 polyclonal antibodies (Martin H, Patel Y, Jones D, Howell S, Robinson K and Aitken A 1993. *Antibodies against the major brain isoforms of 14-3-3 protein. An antibody specific for the N-acetylated amino-terminus of a protein. FEBS Letters.* 331:296-303). The membranes were then incubated with the appropriate secondary horseradish peroxidise conjugated anti-rabbit IgG (Sigma, St Louis, USA) or anti-mouse IgG (Bio-Rad Laboratories, Hercules, USA) antibodies (1:2500 dilution). Immunoreactive proteins were then visualized using the ECL+plus western blotting detection system (Amersham Biosciences, Buckinghamshire, England). Keratinocyte cell lysate (K) was used as a positive control. SF: synovial fluid; PS: patient serum.

Patient Samples

Synovial fluid was obtained from the knee joints of patients with active synovitis prior to the institution of anti-TNF therapeutics. All patients had a DAS score >6.0. Matched blood samples were obtained by standard venipuncture procedures. The clot was removed by centrifugation.

Recombinant 14-3-3 Eta cDNA for keratinocyte-derived 14-3-3 eta was prepared from total RNA extracted from human keratinocytes, cloned and expressed in *E. coli*, and affinity purified, following the methods described in Ghahary et al 2004 J Invest Dermatol 122:1188-1197. Primers used for PCR amplification of the 14-3-3 eta cDNA were SEQ ID NO: 15 (GCGAATTCCTGCAGCGGGCGCGGCTGGCCGA) and SEQ ID NO: 16 (GCTCGAGCCTGAAGGATCTTCAGTTGCCTTC).

Example 1

14-3-3 Expression in Synovial Fluid and Serum of RA Affected Patients

Figure 2:
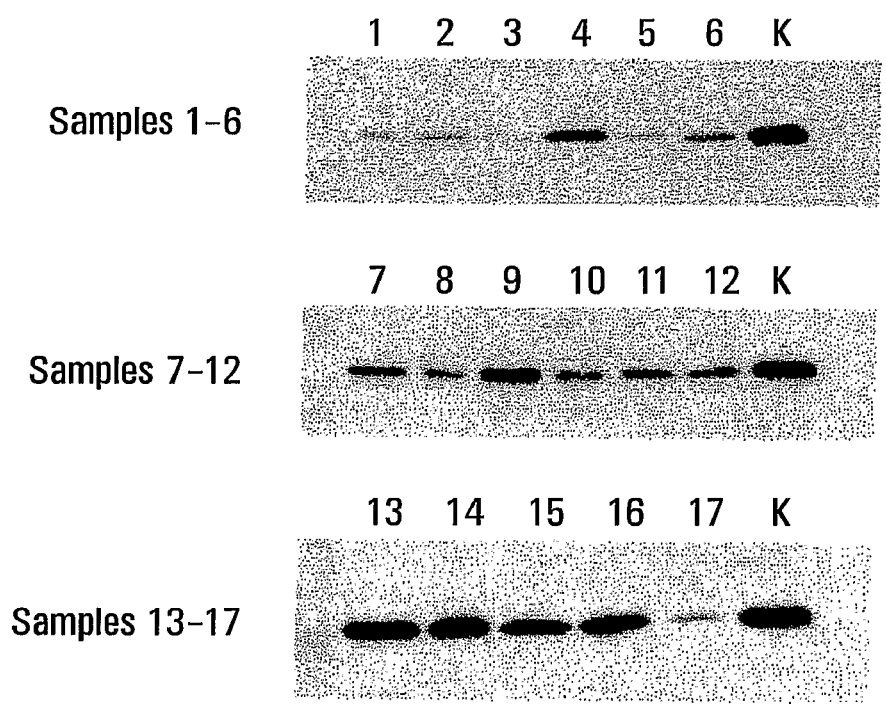

The levels of the different isoforms of 14-3-3 proteins—β, γ, ε, η, τ σ and ζ—in pooled patient synovial fluid (SF) and serum (PS) samples were analyzed by western analysis using keratinocyte cell lysate (K) as a positive control. Only the η and γ isoforms were detected in SF samples, and stained with greater intensity compared to PS. Articular joint synovial fluid samples from 17 RA patients who presented with active synovitis, but had not yet received anti-TNF therapies also exhibited consistent expression of the η isoform of 14-3-3 (FIG. 2). All patients had a disease activity score (DAS) greater than 6.0.

Example 2

MMP Expression in Patient Synovial Fluid Serum

Figure 3:
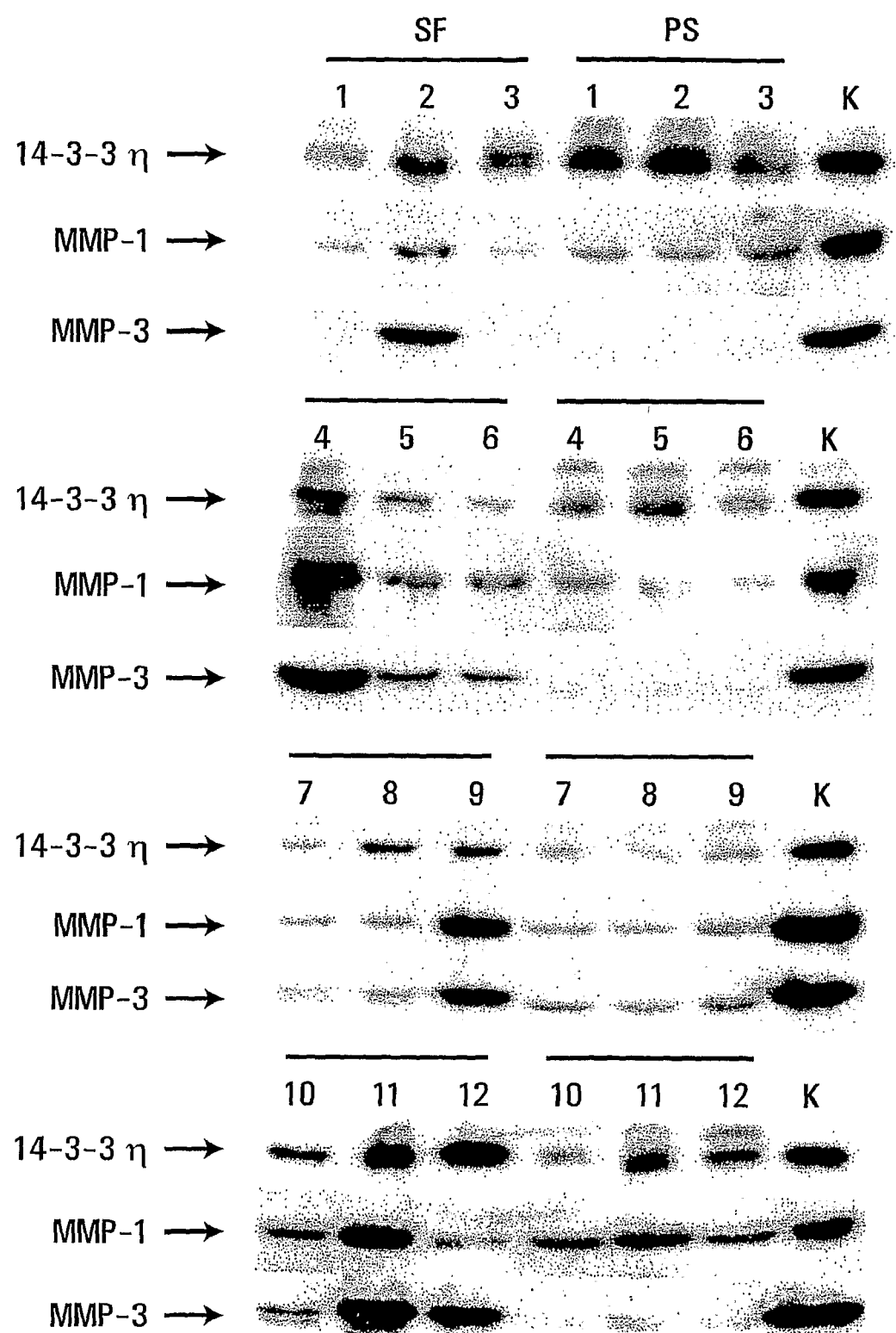
Figure 4:
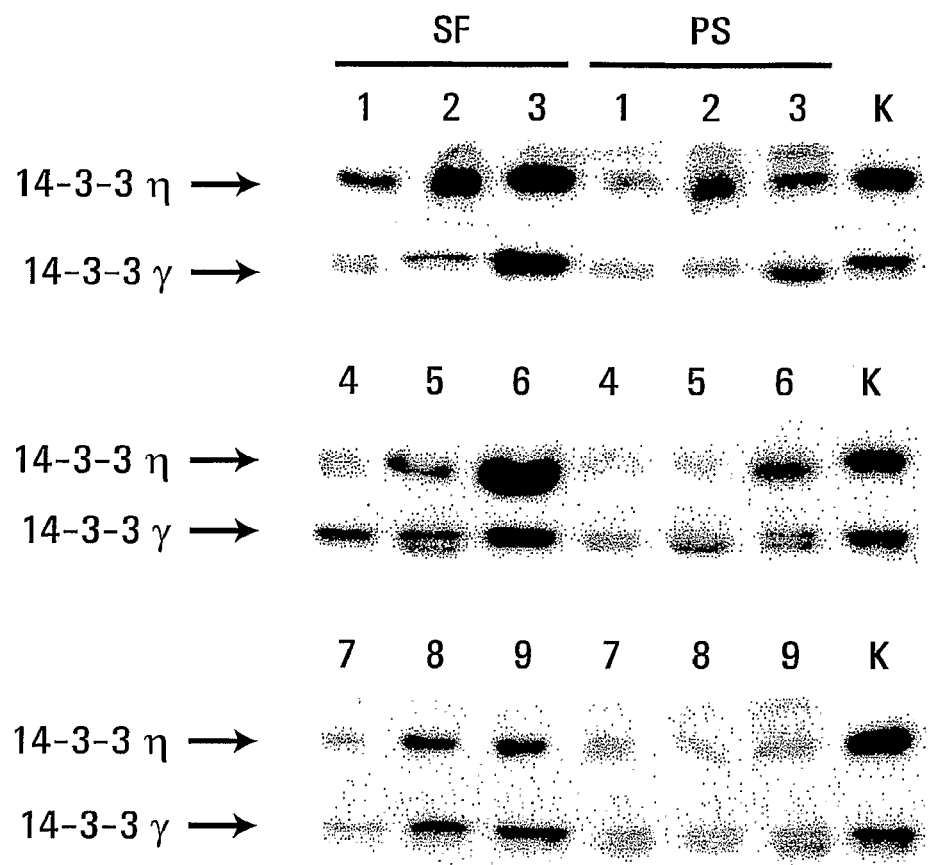
Figure 5:
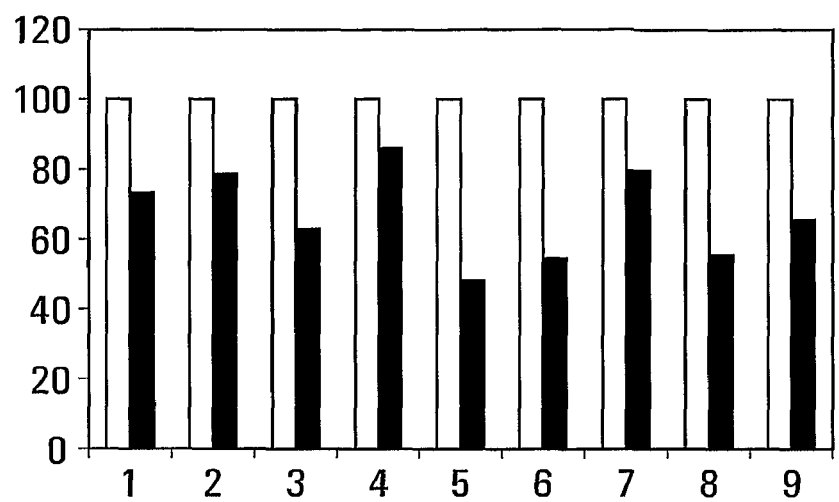

To determine if these variations were correlated to those of MMP-1 and MMP-3 in the same synovial samples, a total of 12 RA synovial fluid samples and their matched serum samples were simultaneously evaluated for 14-3-3η and γ as well as for MMP-1 and MMP-3 proteins (FIG. 3). 14-3-3 η was detected in all samples. MMP-1 was detected in all samples, both SF and PS, while MMP-3 was more variable in the levels detected. The 14-3-3 γ isoform was also detected in patient synovial fluid and serum samples (FIG. 4, 5).

The expression of MMP-1 and MMP-3 demonstrate significant correlation with the expression of the 14-3-3η and γ isoforms in both synovial fluid and serum (Table 1).

TABLE 1

Correlation of MMP and 14-3-3 protein levels in serum and synovial fluid.

| | 14-3-3 η serum | 14-3-3 η synovium | 14-3-3 γ serum | 14-3-3 γ synovium |
|---|---|---|---|---|
| MMP-1 | r = 0.62, p = 0.02 | r = 0.83, p = 0.03 | r = 0.77, p = 0.02 | r = 0.65, p = 0.03 |
| MMP-3 | r = 0.68, p = 0.01 | r = 0.77, p = 0.003 | r = 0.80, p = 0.03 | r = 0.76, p = 0.04 |

Example 3

Figure 6A:
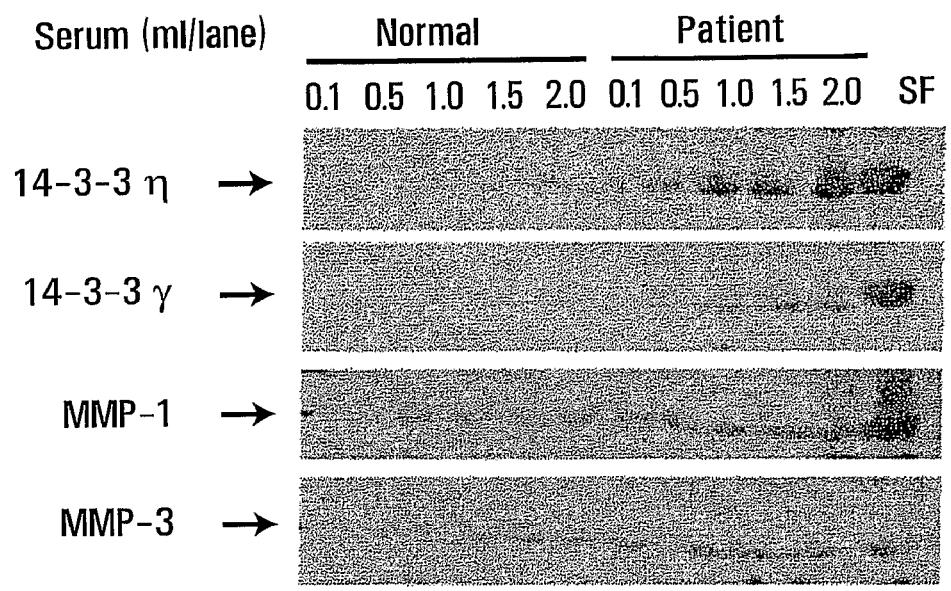

Sensitivity of Western Blot Detection of 14-3-3 Protein in Patient Serum and Synovial Fluid Samples To determine the detection level of 14-3-3 η in synovial fluid and serum samples, samples from 12 RA-affected or normal patients were pooled, and limiting dilutions of the pooled samples were analyzed by western blot. 14-3-3 η was detectable over a range of dilutions—as low as 0.1 µl effective volume of synovial fluid and 1.0 µl effective volume of serum (FIG. 6A).

Figure 6B:
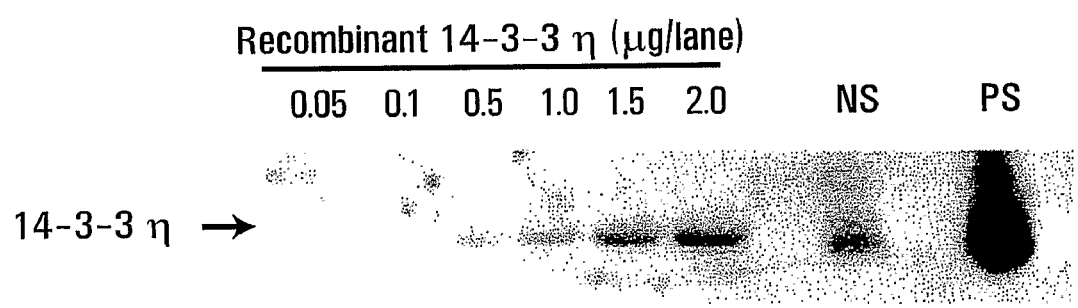

2 µl of pooled normal serum (NS) or patient serum (PS) was run alongside known concentrations of recombinant 14-3-3 η, ranging from 0.05-2.0 µg. The 2 µl volume of NS and PS samples was estimated to have approximately 1-1.5 and 15-20 µg of 14-3-3 η, respectively (FIG. 6B). This suggests that the level of 14-3-3 η occurs in about a 10-fold excess in the serum of RA affected patients, compared to normal patients.

Example 4

Detection of 14-3-3 q Before and After Anti-TNF Therapy

Figure 7:
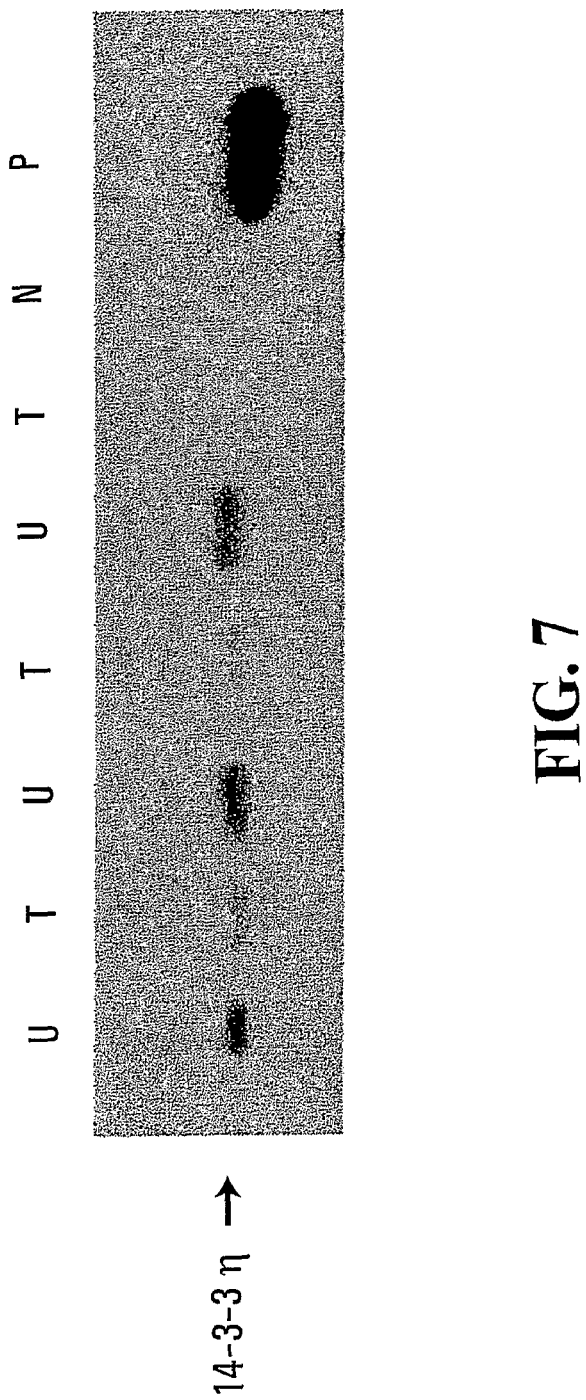

FIG. 7 illustrates the sequential detection of levels of 14-3-3 eta protein in 4 ml of serum samples from RA patients before (U) and after anti-TNF-a (T) Treatment. N=negative control which is 4 ml of a pooled serum sample prepared from 12 serum samples taken from 12 healthy individuals. P=positive control which is 4 mg of keratinocyte cell lysate total protein.

REFERENCES

The following documents are incorporated herein by reference:

1. Harris E D Jr., History and Epidemiology of Rheumatoid Arthritis: How long has it affected us, and who is at risk? In: Rheumatoid Arthritis. Philadelphia: W.B. Saunders Company, 1997: 21-27.
2. Harris E D Jr., Introduction. In: Rheumatoid Arthritis. Philadelphia: W.B. Saunders Company, 1997: xix-xxiii.
3. Harris E D Jr., Rheumatoid Synovium: Complex, and More Than the Sum of its Parts. In: Rheumatoid Arthritis. Philadelphia: W.B. Saunders Company, 1997: 127-149.
5. Firestein G S. (1997). Rheumatoid synovitis and pannus. In: J. H. Klippel and P. A. Dieppe, Editors, Rheumatology, Mosby, London, pp. 5/13.1-5/13.5, 1997.
6. Pap T, Shigeyama Y, Kuchen S. (2000). Arthritis Rheum. 43: 1226-1232.
7. Tolboom T C A, Pieterman E, van der Laan W E. Ann. Rheum. Dis. 61: 975-980, 2002.
8. Sorsa T, Konttinen Y T, Lindy O. Arthritis Rheum. 22: 44-53, 1992.
9. Lindy O, Konttinen Y T, Sorsa T. Arthritis Rheum. 40:1391-1399, 1997.
10. Ahrens D, Koch A E, Pope R M. Arthritis Rheum. 39:1576-1587, 1996.
11. Smeets T J M, Dayer J M, Karan M C. Arthritis Rheum. 43:270-274, 2000.
12. Poole A R; Cartilage in health and disease. In: Koopman W J. Ed. Arthritis and Allied conditions. A textbook of rheumatology. 14th ed. Baltimore: Williams and Wilikins, 2001: 226-284.
13. Konttinen Y T, Ceponis A, Takagi M, Ainola M, Sorsa T, Sutinen M, et al. Matrix Biol. 17:585-601, 1998.
14. Katrib. A, McNeil H P, Youssef P P: Inflamm. Res. 51: 170-175, 2002.
15. Harris E D Jr., Cytokines, Lymphokines, Growth Factors, and Chemokines. In: Rheumatoid Arthritis. Philadelphia: W.B. Saunders Company, 1997: 105-125.
16. Jasser, M. Z., Mitchell P. G. and Cheung, H. S.: induction of stomelysin-1 and collagenases synthesis in fibrochondrocytes by TNF-alpha. Matrix Biology 14: 241, 1994.
17. Burger D, Rezzonico R, Li J M, Modoux C, Pierce R A, Welgus H G, Dayer J M. Arthritis Rheum. 41(10):1748-59, 1998
18. Y. Yamamura, R. Gupta, Y. Mont, X. He, R. Pai, J. Endres, A. Freiberg, K. Chung and D. A. Fox. J. Immunol. 166 (2001), pp. 2270-2275
19. Miranda-Carus M E, Balsa A, Benito-Miguel M, Perez de Ayala C, Martin-Mola E. J. Immunol. 173:1463-1476, 2004
20. Cho M L, Yoon C H, Hwang C Y. Arthritis Rheum. 50:776-784, 2004
21. Bombara M P, Webb D L, Conrad P. J. Leukocyte Biol. 54: 399-406, 1993.
22. McInnes I B, Leung B P, Liew F Y. Arthritis Res. 2(5):374-8.34, 2000.
23. FU H, Subramanian R R, Masters S C: Annu Rev Pharmacol Toxicol 40:617-647, 2000.
24. Hsich G, Kenney K, Gibbs C J, Lee K H, Harrington M G: N Engl J Med 335:924-30, 1996
25. Wilker E, Yaffe M B: J Mol Cell Cardiol 37: 633-642, 2004.
26. Moore et al. 1967.
27. Ichimura T, Isobe T, Okuyama T, Yamauchi T, Fujisawa H (1987) FEBS Lett. 219:79-82.
28. Ichimura T, Isobe T, Okuyama T, Takahashi N, Araki K, Kuwano R, Akahashi Y (1988). Proc Natl Acad Sci USA, 85:7084-8.
29. Toker A, Ellis C A, Sellers L A, Atiken A 1990. Eur J Biochem 191:421-429.
30 Craparo A, Freund R, Gustafson T (1997). J Biol Chem 272:11663-69.
31. Yaffe M B (2002). FEBS Lett 513(1):53-57.
32. Hermeking H, Lengauer C, Polyak K, He T C, Zhang L, Thiagalingam S, Kinzler K W, Volgelstein B. Mol Cell 1:3-11, 1997.
33. Chan T A, Hermeking H, Lengauer C, Kinzler K W, Volgelstein B. Nature 401:616-620, 1999.
34. Laronga C, Yang H Y, Neal C, Lee M H (2000). J. Biol. Chem. 275:23106-23112.
35. Boston P F, Jackson P, Thompson R J. J. Neurochem. 38, 1475-82, 1982.
36. Katz A B, Taichman, L B. J Invest Dermatol 112:818-821, 1999.
37. Ghahary A, Karimi-Busheri F, Marcoux Y, Li Y, Tredget E E, Kilani R T, Li L, Zheng J, Karami A, Keller B, Weinfeld M. J. Invest. Dermatol. 122(5): 1188-1197, 2004.
38. Ghaffari A, Li Y, Karami A, Ghaffari M, Tredget E E, Ghahary A. J. Cell. Biochem. January 2006.

While specific embodiments of the invention have been described and illustrated, such embodiments should be considered illustrative of the invention only and not as limiting the invention as construed in accordance with the accompanying claims.

The invention claimed is:

1. A method of detecting the eta isoform of the 14-3-3 protein in a patient, said method comprising:
   a. obtaining a test sample from a human patient at risk or suspected of having an inflammatory disorder of the joints of the body, wherein the test sample is selected from the group consisting of blood, serum, plasma, and synovial fluid; and
   b. detecting whether 14-3-3 eta protein is present in the test sample by contacting the test sample with an anti-14-3-3 eta protein antibody and detecting binding between 14-3-3 eta protein and the antibody.

2. The method according to claim 1, wherein said detecting comprises ELISA or western blotting.

3. The method according to claim 1, wherein said 14-3-3 eta isoform comprises the amino acid sequence of SEQ ID NO: 3.

4. The method according to claim 1, further comprising detecting at least one additional protein in said test sample.

5. The method according to claim 4, wherein said at least one additional protein is a matrix metalloproteinase.

6. The method according to claim 2, wherein said detecting comprises ELISA.

7. The method according to claim 6, wherein said sample is serum.

8. A method of detecting the eta isoform of the 14-3-3 protein in a patient, said method comprising:
   a. obtaining a test sample from a human patient having pain, swelling, and stiffness in the joints of the body, wherein the test sample is selected from the group consisting of blood, serum, plasma, and synovial fluid; and
   b. detecting whether 14-3-3 eta protein is present in the test sample by contacting the test sample with an anti-14-3-3 eta protein antibody and detecting binding between 14-3-3 eta protein and the antibody.

9. The method according to claim 8, wherein said detecting comprises ELISA or western blotting.

10. The method according to claim , wherein said 14-3-3 eta isoform comprises the amino acid sequence of SEQ ID NO: 3.

11. The method according to claim 8, further comprising detecting at least one additional protein in said test sample.

12. The method according to claim 11, wherein said at least one additional protein is a matrix metalloproteinase.

13. The method according to claim 9, wherein said detecting comprises ELISA.

14. The method according to claim 13, wherein said sample is serum.

\* \* \* \* \*